(12) United States Patent
Silva (10) Patent No.: US 8,857,265 B2
(45) Date of Patent: Oct. 14, 2014

(54) SYSTEM AND METHOD FOR ALIGNING A TEST ARTICLE WITH A LOAD

(75) Inventor: Jose Rafael Silva, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 297 days.

(21) Appl. No.: 13/346,554

(22) Filed: Jan. 9, 2012

(65) Prior Publication Data

US 2013/0174665 A1 Jul. 11, 2013

(51) Int. Cl.
*G01N 3/00* (2006.01)

(52) U.S. Cl.
USPC .......................................................... 73/788

(58) Field of Classification Search
USPC ................................................... 73/760, 788
See application file for complete search history.

(56) References Cited

U.S. PATENT DOCUMENTS

| | | | |
|---|---|---|---|
| 3,320,798 A * | 5/1967 | Gram | 73/857 |
| 4,436,268 A * | 3/1984 | Schriever | 248/188.3 |
| 5,007,175 A | 4/1991 | Schwarz | |
| 5,377,549 A * | 1/1995 | Werner | 73/860 |
| 5,861,956 A * | 1/1999 | Bridges et al. | 356/614 |
| 7,462,007 B2 * | 12/2008 | Sullivan et al. | 411/231 |
| 7,679,845 B2 | 3/2010 | Wang | |
| 8,544,338 B2 * | 10/2013 | Pettit | 73/811 |
| 2009/0158879 A1 | 6/2009 | Viola | |

OTHER PUBLICATIONS

Wikipeida, "Universal testing machine", available at <http://en.wikipedia.org/wiki/Universal_testing_machine>, last visited Jan. 8, 2011.

* cited by examiner

*Primary Examiner* — Lisa Caputo
*Assistant Examiner* — Octavia Hollington (57) ABSTRACT

An apparatus for orienting a test article relative to a loading axis includes a first member and a second member. The first member may have a concave surface. The second member may have a convex surface configured to engage the concave surface in a manner such that the second member is movable relative to the first member. The test article may be coupled to one of the first and second members such that relative movement thereof facilitates general alignment of the test article with the axial loading axis. The leveling apparatus may further include a plurality of positioning devices configured to facilitate adjustment of an orientation of the second number relative to the first member such that the alignment of the test article may be adjusted.

20 Claims, 10 Drawing Sheets

SYSTEM AND METHOD FOR ALIGNING A TEST ARTICLE WITH A LOAD

FIELD

The present disclosure relates generally to testing fixtures and, more particularly, to the aligning of a test article with an applied load.

BACKGROUND

Structural components are typically tested to verify their load-carrying capability and confirm the integrity of the component design. A test article representing the structural component may be mounted in a testing machine and subjected to test loads in a controlled environment to simulate loads to which the component may be subjected when in service. For example, test loads may be applied to a test article representing a component of an aircraft. Test loads may be applied to the test article during static and/or fatigue testing to simulate in-flight aerodynamic loads, landing loads, and other loads that may act on the component during its operational life.

During testing, the test article may be monitored to determine the response of the test article to test loads. For example, the test article may be instrumented with sensors at different locations so that the stress distribution in the test article may be determined. The stress measurements may be compared to predicted stresses at each location. The stress predictions may be determined by stress analysis of the component. In this regard, the measured stress data may be used to verify and validate the structural design of the test article and/or to validate the stress analysis methodology. The test data may also be used to obtain certification for the component and/or the aircraft.

For accurate simulation of a load to which a component may be subjected in service, it is typically necessary to mount the test article in the test fixture such that the test article is substantially aligned with the test load. Unfortunately, due to manufacturing tolerances associated with the fabrication of the test article or due to tolerances associated with the testing machine, the test article may be misaligned with the test load. Misalignment of the test load with the test article may lead to eccentric loading of the test article which may produce stresses in the test article that may not be representative of the actual loads to which a component may be subjected when in service.

As can be seen, there exists a need in the art for a system and method for mounting a test article in a testing machine such that test article may be aligned with the test load.

SUMMARY

The above-noted needs associated with alignment of a test article with a test load are specifically addressed and alleviated by the present disclosure which provides a leveling apparatus having a first member and a second member. The first member has a concave surface. The second member has a convex surface that may be configured to engage the concave surface in a manner such that the second member is movable relative to the first member. The test article may be coupled to one of the first and second members such that relative movement thereof facilitates general alignment of the test article with a loading axis of an axial load that may be applied to the test article. The leveling apparatus may include a plurality of positioning devices configured to facilitate adjustment of an orientation of the second member relative to the first member for adjusting the alignment of the test article with the axial loading axis.

In a further embodiment, disclosed is a testing machine for applying a compressive load to a test article. The testing machine may include an axial load actuator configured to apply a compressive load to a test article along an axial loading axis. The testing machine may include a leveling apparatus having a first member and a second member. The first member may have a concave surface. The second member may have a convex surface that may be configured to engage the concave surface in a manner such that the second member is movable relative to the first member. The test article may be coupled to one of the first and second members such that relative movement thereof facilitates general alignment of the test article with the axial loading axis. The leveling apparatus may include a plurality of positioning devices configured to facilitate adjustment of an orientation of the second member relative to the first member for adjusting the alignment of the test article with the axial loading axis.

Also disclosed is method of aligning a test article with a loading axis. The method may include coupling the test article to a leveling apparatus which may comprise a first member and a second member. The first member may have a concave surface. The second member may have a convex surface that may be engaged to the concave surface. The method may include applying an initial axial load to the test article and moving the convex surface relative to the concave surface in response to the application of the axial load such that the second member is reoriented relative to the first member. The method may additionally include aligning the test article with the axial loading axis in response to reorienting the second member relative to the first member. The method may also include adjusting at least one positioning device of the leveling apparatus to adjust the orientation of the second member relative to the first member, and adjusting the alignment of the test article relative to the axial loading axis in response to adjusting the positioning device.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
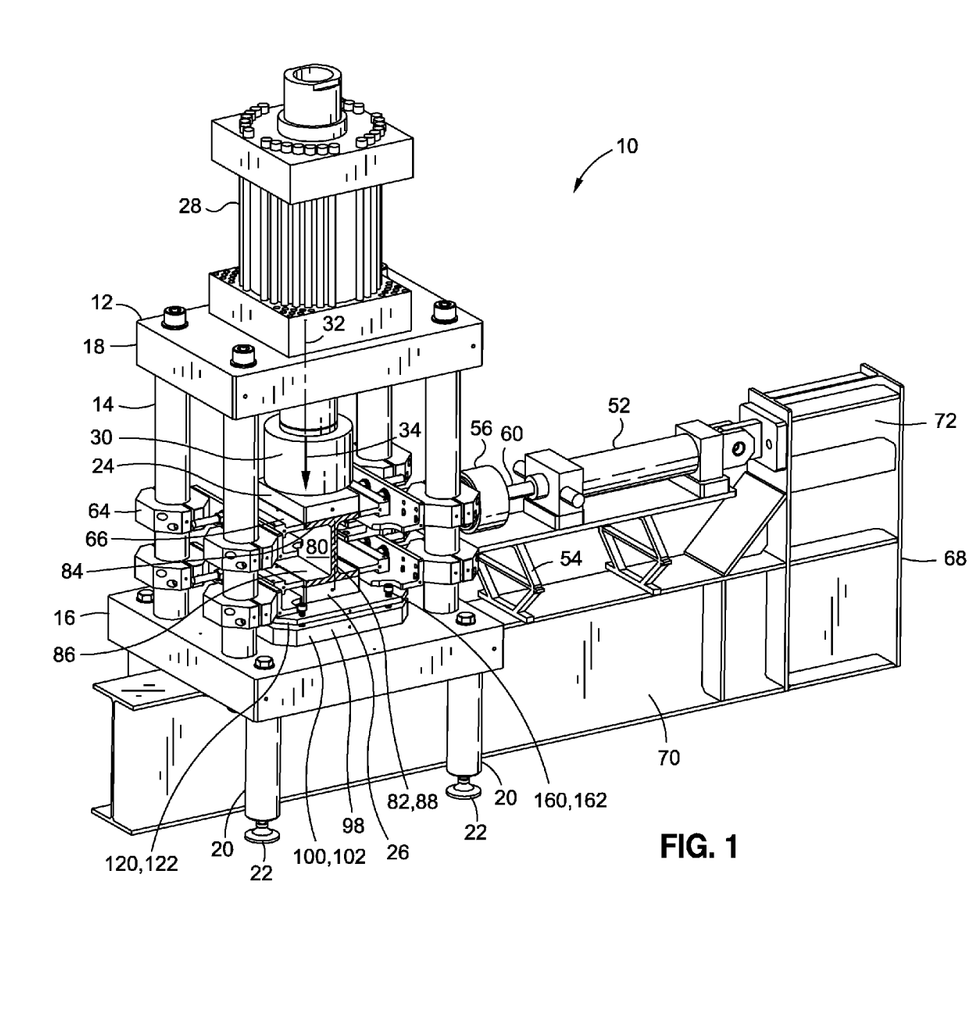
FIG. 1 is a perspective illustration of a universal testing machine having a side load reaction frame coupled thereto for side load capability and further illustrating a test article mounted between an upper loading plate and a lower loading plate and wherein the lower loading plate is mounted on a leveling apparatus.
Figure 10:
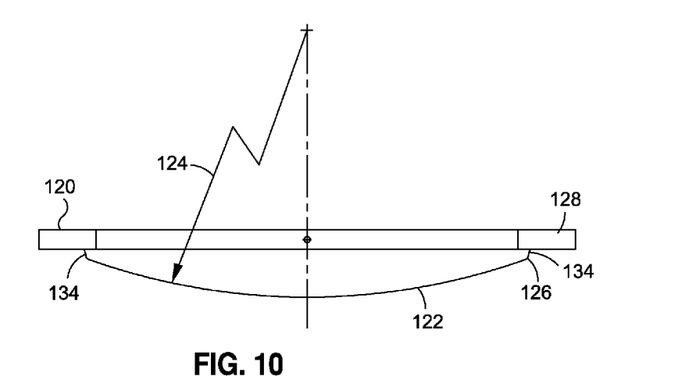
FIG. 10 is a side view of the second member taken along line 10 of FIG. 9.

Referring now to the drawings wherein the showings are for purposes of illustrating preferred and various embodiments of the disclosure, shown in FIG. 1 is a perspective illustration of an embodiment of a testing machine 10. The testing machine 10 may incorporate a leveling apparatus 98 for orienting a test article 80 relative to an axial loading axis 32 of an axial load 34 that may be applied to the test article 80. The leveling apparatus 98 may include a first member 100 having a hemispherical concave surface 102 (FIG. 8) and a second member 120 having a hemispherical convex surface 122 (FIG. 10). The concave surface 102 may be directly engaged to the convex surface 122 at an interface 140 (FIG. 6) such that the concave surface 102 and convex surface 122 may be universally movable relative to one another.

Referring to FIG. 1, the test article 80 may be directly or indirectly supported by the leveling apparatus 98. For example, the test article 80 may be directly mounted (not shown) to the leveling apparatus 98. Alternatively, the test article 80 may be mounted to a loading plate 24 which may be mounted to the leveling apparatus 98. Although the present disclosure describes the test article 80 or lower loading plate 26 as being coupled to the second member 120 (having a convex surface 122), the leveling apparatus 98 may be flipped 180 degrees and installed such that the test article 80 or lower loading plate 26 may be coupled to the first member 100 (having a concave surface 102). In the flipped arrangement, the second member 120 (having a convex surface 122) may be mounted to the tabletop 16 of the testing machine 10.

It should also be noted that although the leveling apparatus 98 is described and illustrated as being mounted between the tabletop 16 of the universal testing machine 10 and the proximal end 92 (FIG. 2) of the test article 80, the present disclosure contemplates that the leveling apparatus 98 may be mounted above (not shown) the test article 80 between the axial load actuator 28 and the distal end 94 (FIG. 2) of the test article 80. Furthermore, the present disclosure contemplates that a leveling apparatus 98 may be mounted on each one of the proximal and distal ends 92, 94 of the test article 80 and is not limited to a single leveling apparatus 98 mounted to one of the ends 92, 94 of the test article 80. Additional leveling apparatuses (not shown) may also be mounted to other locations on the test article 80. In this regard, leveling apparatuses (not shown) may be mounted at any location wherein it is desired to align a loading axis with a test article.

Advantageously, relative movement of the concave and convex surfaces 102, 122 (FIG. 3) of the leveling apparatus 98 (FIG. 1) provides a means for aligning the test article 80 (FIG. 1) with a load such as an axial compression load 34 (FIG. 1) that may be applied to the test article 80 by the testing machine 10 (FIG. 1). Upon application of the axial load 34 to the test article 80, the first and second members 100, 120 may be reoriented relative to one another as the concave and convex surfaces 102, 122 slide along the interface 140 (FIG. 6) between the concave and convex surfaces 102, 122. The reorientation of the first and second members 100, 120 may result in the test article 80 self-aligning with the axial loading axis 32 (FIG. 1) as the axial load 34 is applied to the test article 80. Advantageously, the leveling apparatus 98 may include three or more positioning devices 160 for fine-tuning or adjusting the alignment of the test article 80 relative to the axial loading axis 32 as described in greater detail below.

In FIG. 1, the leveling apparatus 98 is shown implemented for use in a universal testing machine 10 as may be used for structural testing of materials, components, and assemblies. In this regard, the leveling apparatus 98 may be implemented for use in compressive static testing, compressive fatigue testing, and any other type of compressive testing, without limitation, including, vibration, shock, and acoustic testing. Further in this regard, the leveling apparatus 98 disclosed herein may be implemented for use in any type of testing environment or testing application wherein alignment of a test article with a compressive loading axis is desired. Although the leveling apparatus 98 is described in the context of supporting a test article 80 having an I-beam configuration including a web 88 interconnecting upper and lower flanges 84, 86, the leveling apparatus 98 may be configured for supporting any one of a wide variety of test article configurations, without limitation. Advantageously, the leveling apparatus 98 may improve the accuracy of test results due to the increased accuracy in aligning the test article 80 with a loading axis. In addition, the leveling apparatus 98 may significantly reduce the amount of time required to set up and align the test article 80 with a loading axis due to the self-aligning capability of the leveling apparatus 98.

Figure 2:
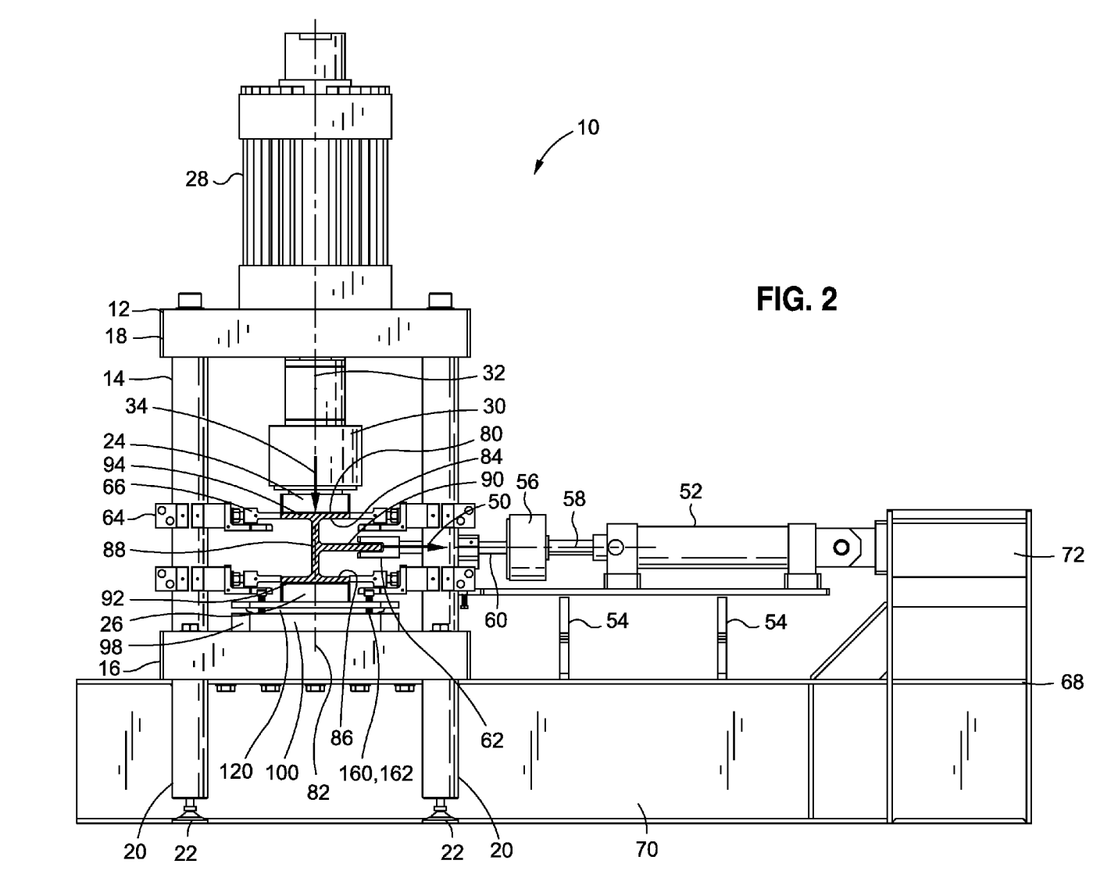
FIG. 2 is a side view illustration of the universal testing machine with side load capability and having the test article mounted between the upper loading plate and the lower loading plate with the lower loading plate being mounted on the leveling apparatus.
Figure 3:
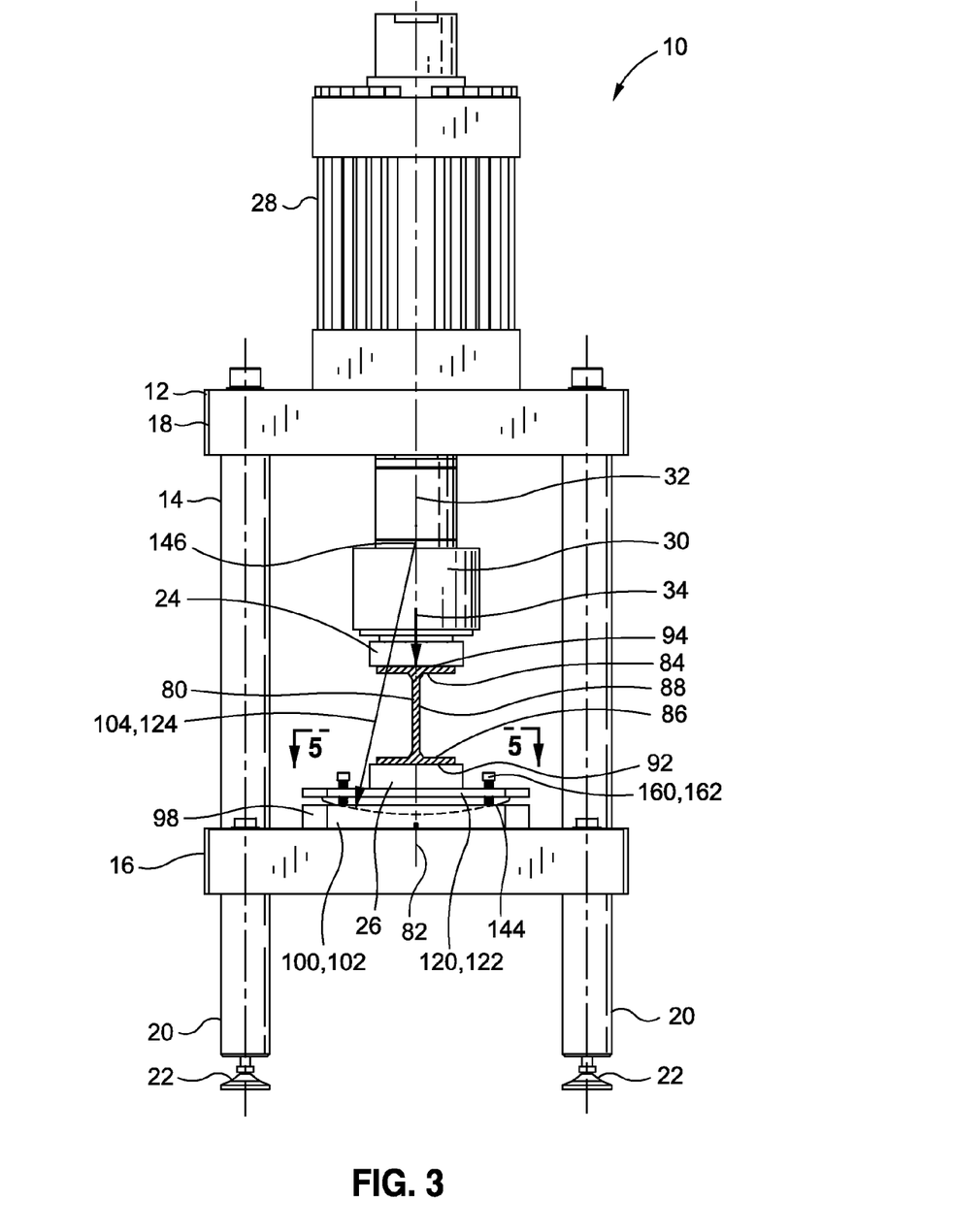
FIG. 3 is a side view illustration of the universal testing machine with the side load reaction frame omitted for clarity and illustrating the leveling apparatus comprised of a first member and a second member.

Referring to FIGS. 1-3, shown is the universal testing machine 10 which may include a relatively rigid frame assembly 12. The frame assembly 12 may comprise a tabletop 16 supported by a plurality of legs 20. The legs 20 may include feet 22 which may be mounted on a surface such as a bench or a floor of a test laboratory. The universal testing machine 10 may include a plurality of posts or columns 14 extending upwardly from the tabletop 16. An upper brace or crosshead 18 may be supported by the columns 14. An axial load actuator 28 may be supported on the crosshead 18. The axial load actuator 28 may be configured to provide compressive loading of a test article 80 mounted to the tabletop 16. The axial load actuator 28 may be hydraulically or electromechanically powered or the axial load actuator 28 may be powered by other suitable means.

The testing machine 10 may include an axial load measuring device 30 such as a load cell for measuring the magnitude of the axial load 34 applied to the test article 80. The test article 80 may be mounted between upper and lower loading plates 24, 26. The upper and lower loading plates 24, 26 may be sized and configured to substantially uniformly distribute the axial load 34 into the test article 80. In this regard, the upper and lower loading plates 24, 26 may have a relatively high stiffness for transmitting the load from the axial load actuator 28 into the test article 80 with minimal flexure or bending of the loading plates 24, 26. Although FIG. 1-3 illustrate the test article 80 mounted between upper and lower loading plates 24, 26, it is contemplated that the test article 80 may be mounted directly to the leveling apparatus 98 as indicated above and the axial load 34 may be applied directly to the test article 80 from the axial load actuator 28.

FIGS. 1-2 further illustrate a side load reaction frame 68 that may be coupled to the universal testing machine 10. The side load reaction frame 68 may include a horizontal portion 70 that may be fixedly coupled to the tabletop 16 of the testing machine 10. The side load reaction frame 68 may include a vertical portion 72 that may provide an attach point for a side load actuator 52. The side load actuator 52 may be included with the universal testing machine 10 for applying a side load 50 to the test article 80 such as during application of the axial compressive load 34. The side load actuator 52 may be supported by one or more actuator supports 54. A side load measuring device 56 such as a load cell may be coupled to the side load actuator 52 for measuring the magnitude of the side load 50 applied to the test article 80. The side load measuring device 56 may be mounted to an actuator rod 60 extending from the side load actuator 52. The actuator rod 60 may include a clevis fitting 62 (FIG. 2) for attachment to a lug 90 (FIG. 2) that may be affixed to the test article 80. To prevent lateral movement of the test article 80 during application of a side load 50, one or more bumper assemblies 66 may be affixed to the columns 14 of the universal testing machine 10 by means of a plurality of side load clamps 64. It should be noted that the side load actuator 52 is an optional component of the universal testing machine and is described herein as a means to illustrate the functionality of the leveling apparatus 98.

Referring to FIG. 3, shown is a side view of the universal testing machine with the side load actuator 52 (FIG. 2) and the side load reaction frame 68 (FIG. 2) omitted for clarity. The test article 80 is shown mounted between the upper loading plate 24 and the lower loading plate 26. The lower loading plate 26 may be mounted on the leveling apparatus 98. The leveling apparatus 98 may include the first member 100 which may be non-movably coupled to the tabletop 16 of the universal testing machine 10. The first member 100 may include the concave surface 102. The second member 120 may include the convex surface 122 which may be placed in direct engagement with the concave surface 102 of the first member 100.

The leveling apparatus 98 may include a plurality of positioning devices 160 for adjusting the orientation of the second member 120 relative to the first member 100. Although shown as being mounted (e.g., threadably engaged) to the second member 120, the positioning devices 160 may optionally be mounted to the first member 100. In the configuration shown in FIG. 6, the positioning devices 160 may be configured to engage the first member 100 by placing the tips 164 of the positioning devices 160 into contact with the first member 100. The positioning devices 160 may facilitate the adjustment of the orientation of the second member 120 relative to the first member 100. Once adjusted, the positioning devices 160 may maintain the orientation of the second member 120 relative to the first member 100 and prevent relative movement thereof during the application of an axial compression load 34 to the test article 80 as described in greater detail below.

Figure 4:
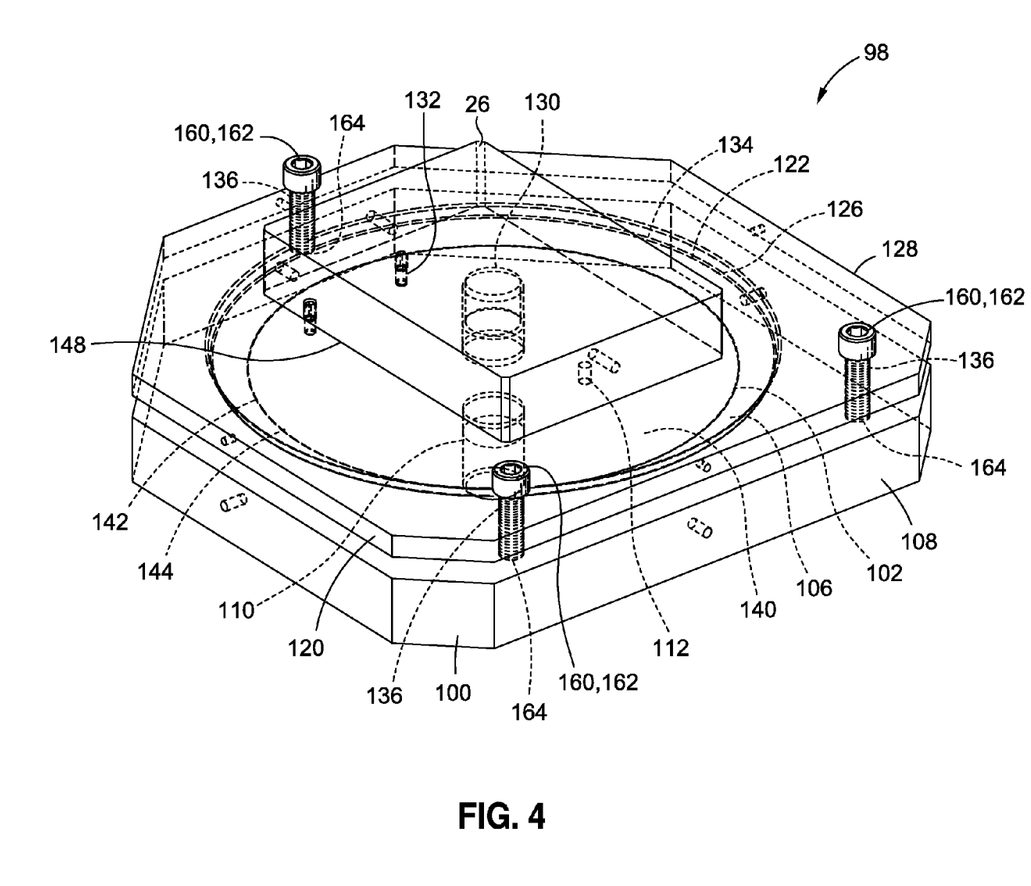
FIG. 4 is a perspective illustration of the leveling apparatus showing the first member engaged to the second member.

Referring to FIG. 4, shown is a perspective illustration of the leveling apparatus 98 comprised of the first and second members 100, 120 and having a lower loading plate 26 mounted to the second member 120. In an embodiment, the first member 100 and/or the second member 120 may be configured as a unitary structure. For example, each one of the first and second members 100, 120 may be formed of a homogenous metallic material. However, the first member 100 and/or second member 120 may be formed of a nonmetallic material or as a hybrid of metallic and nonmetallic material. In addition, the first member 100 and/or the second member 120 may be formed as an assembly of one or more components and are not limited to being formed as a unitary structure.

In FIG. 4, the positioning devices 160 are shown mounted to the second member 120. In the embodiment shown, the positioning devices 160 are configured as screws 162 such as Allen head screws that may be threadably engaged to a corresponding number of threaded bores 136 formed in the second member 120. However, the positioning devices 160 may be configured as any one of a wide variety of configurations and are not limited to being formed as threaded screws 162. Furthermore, the positioning devices 160 are not limited to being threadably engaged to the second member 120. For example, the positioning devices 160 may be threadably engaged to the first member 100 and may be extended such that the tips 164 of the positioning devices 160 may be placed into contact with the second member 120 for adjusting the orientation of the first member 100 relative to the second member 120.

Figure 5:
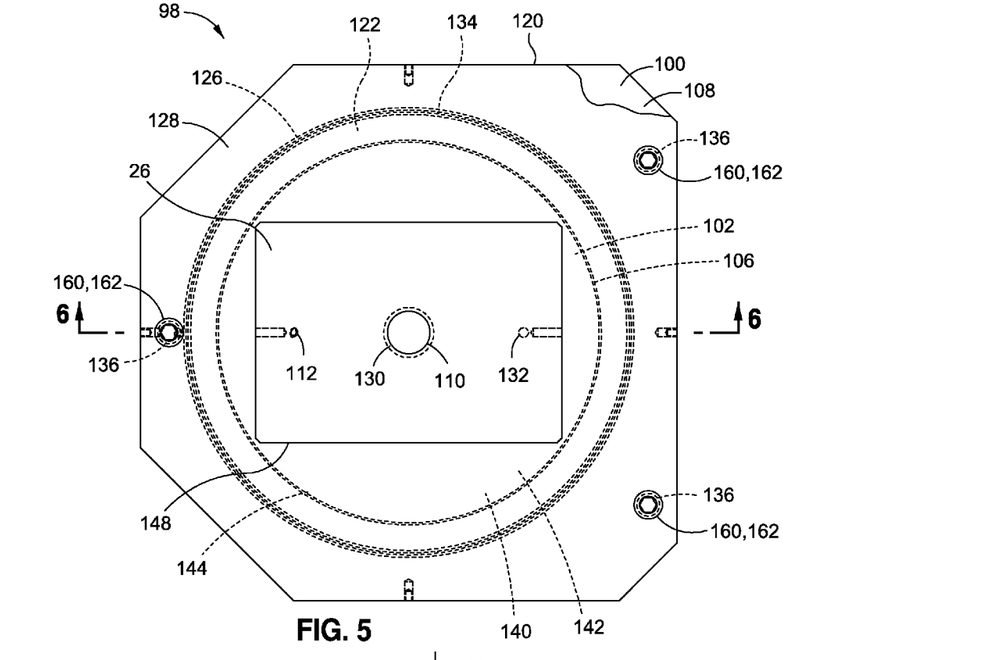
FIG. 5 is a top view of the leveling apparatus.

Referring to FIG. 5, shown is a top view of the leveling apparatus 98 illustrating the lower loading plate 26 mounted to the second member 120. The first member 100 and the second member 120 are shown as having orthogonal profile shapes with chamfered corners. However, the first member 100 and the second member 120 may be provided in any one of a wide variety of profile shapes. For example, the first member 100 and/or the second member 120 may be formed in a circular profile shape or in any other profile shape, without limitation. In addition, the first member 100 may be provided in a profile shape that is different than the profile shape of the second member 120.

The positioning devices 160 are shown as being positioned along edges of the second member 120. Although three positioning devices 160 are shown, any number of positioning devices 160 equal to or greater than three may be provided. The positioning devices 160 are shown as being spaced about the perimeter 106, 126 of the concave and convex surfaces 102, 122. However, the positioning devices 160 may be mounted at a variety of different locations within the leveling apparatus 98 that will facilitate the adjustment of the orientation of the second member 120 relative to the first member 100 and are not limited to being positioned in the locations on the perimeter 106, 126 of the concave and convex surfaces 102, 122 shown in FIG. 5. The positioning devices 160 are configured to facilitate adjustment of the orientation of the first member 100 relative to the second member 120 as a means to adjust the alignment of the test article 80 relative to the axial loading axis 32 of the universal testing machine 10. However, the positioning devices 160 may facilitate adjustment of the orientation or alignment of the test article 80 such that stresses in the test article 80 resulting from the application of an axial load 34 may be distributed through the test article 80 in a predicted or desired manner as described in greater detail below.

Referring still to FIG. 5, the concave surface 102 of the first member 100 defines the perimeter 106. Likewise, the convex surface 122 of the second member 120 also defines a perimeter 126. In the embodiment shown, the perimeter 126 of the convex surface 122 is larger in diameter than the perimeter 106 of the concave surface 102. However, it is contemplated that the leveling apparatus 98 may be configured such that the perimeter 106 of the concave surface 102 is larger in diameter than the perimeter 126 of the convex surface 122. Advantageously, the concave surface 102 and the convex surface 122 may also be configured such that the interface 140 between the concave and convex surfaces 102, 122 defines an interface perimeter 144 having a size or diameter that circumscribes the area 148 of the loading plate 26 in contact with the second member 120 when the leveling apparatus 98 is viewed along the axial loading axis 32. For applications wherein the upper and/or lower loading plate 24, 26 is omitted (not shown) from the universal testing machine 10, the concave surface 102 and the convex surface 122 may be configured such that the interface perimeter 144 circumscribes the area 148 of the proximal end (not shown) of the test article 80 in contact with the second member 120.

By configuring the leveling apparatus 98 such that the interface perimeter 144 is larger in size (e.g., larger in diameter) than the area 148 of the test article 80 or the lower loading plate 26, the test article 80 and/or the lower loading plate 26 may be fully supported by the concave and convex surfaces 102, 122. In this manner, the axial load 34 applied to the test article 80 may have a direct load path from the test article 80 into the interface 140 between the concave and convex surfaces 102, 122 with substantially no unsupported areas of the test article 80 or loading plate 26. In this regard, the leveling apparatus 98 is configured to eliminate bending in the second member 120 which may otherwise occur if the area 148 of the test article 80 or loading plate 26 extended outside of the interface perimeter 144. In addition, the concave and convex surfaces 102, 122 may be provided with a radius of curvature 104, 124 (FIG. 6) such that the axial load 34 (FIG. 3) on the test article 80 (FIG. 3) is always directly supported by the concave and convex surfaces 102, 122. In this manner, the first and second members 100, 120 are inherently stable with no moments that would otherwise cause the first and second members 100, 120 to move under load.

Figure 6:
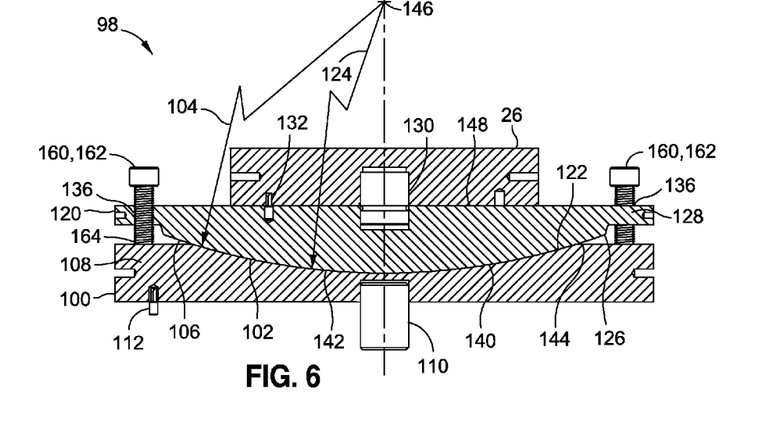
FIG. 6 is a cross sectional illustration of the leveling apparatus and illustrating a convex surface of the second member engaged to a concave surface of the first member and further illustrating positioning devices configured to facilitate adjustment of the orientation of the second member relative to the first member to adjust the alignment of the test article relative to an axial loading axis.

In FIG. 6, shown is a cross-sectional illustration of the leveling apparatus 98 having the lower loading plate 26 mounted to the second member 120 and the second member 120 engaged to the first member 100. The lower loading plate 26 may be laterally coupled to the second member 120 by means of a centering pin 130. One or more anti-rotation pins 132 may likewise be included at the junction between the lower loading plate 26 and the second member 120 to prevent rotation of the lower loading plate 26 relative to the second member 120. However, the lower loading plate 26 may be mounted to the second member 120 by any means and is not limited to the use of a centering pin 130 and/or anti-rotation pins 132. The first member 100 may likewise be non-movably coupled to the tabletop 16 (not shown) by means of a centering pin 110 and one or more anti-rotation pins 112 or by other suitable means to prevent movement of the first member 100 relative to the tabletop 16 (FIG. 3).

In FIG. 6, the convex surface 122 may have a radius of curvature 124 that is substantially equivalent to the radius of curvature 104 of the concave surface 102. For example, the difference in the radius of curvature 104 of the concave surface 102 and the radius of the curvature 124 of the convex surface 122 may be no greater than approximately 0.005 inch to minimize the amount of free play between the first and second members 100, 120. However, the first and second members 100, 120 may be provided with radii of curvature 104, 124 that differ by an amount greater than approximately 0.005 inch. By minimizing the amount of free play between the concave surface 102 and the convex surface 122, flexing or bending of the second member 120 may be minimized which may improve the accuracy of the compression testing of the test article 80.

Referring briefly to FIG. 3, the radii of curvature 104, 124 of the concave surface 102 and the convex surface 122 may have a center of curvature 146 that may be located at a point along the axial loading axis 32. For example, the concave surface 102 and the convex surface 122 may be configured such that the center of curvature 146 may be located above the distal end 94 of the test article 80 as shown in FIG. 3. By locating the center of curvature 146 above the distal end 94 of the test article 80, the positioning devices 160 may provide a desired level of sensitivity for adjusting the orientation of the second member 120 relative to the first member 100. However, the center of curvature 146 of the concave surface 102 and convex surface 122 may be located at any location along the axial loading axis 32 of the test article 80. The concave and convex surfaces 102, 122 may be provided with a relatively large radius of curvature 104, 124 to provide a correspondingly small degree of sensitivity for adjusting the orientation of the second member 120 relative to the first member 100 using the positioning devices 160. The positioning devices 160 or positioning screws 162 may also be provided with a thread pitch (not shown) that may provide a desired level of sensitivity for adjusting the orientation of the second member 120 relative to the first member 100. The concave surface 102 and the convex surface 122 may also be provided with radii of curvature 104, 124 such that a resultant (not shown) of a reaction force (not shown) against the axial load 34 may pass through the interface 140 (FIG. 6) (i.e., within the interface perimeter 144—FIG. 6) between the concave surface 102 and the convex surface 122. In this manner, the axial load 34 may have a direct load path into the interface 140 with no unsupported areas of the test article 80 or loading plate 24 which may otherwise cause bending of the second member 120.

Referring to FIG. 6, the concave surface 102 and the convex surface 122 may preferably be provided with a surface roughness that minimizes sliding friction at the interface 140 and facilitates relative sliding motion between the concave surface 102 and the convex surface 122. In an embodiment, the concave surface 102 and the convex surface 122 may have a surface roughness of no greater than approximately 32 micro-inch. However, the concave surface 102 and the convex surface 122 may be provided with a surface roughness of greater than 32 micro-inch which may reduce the cost and time for fabrication of the first and second member 120, 122. The leveling apparatus 98 may further include a layer of lubricant 142 between the first member 100 and the second member 120 to facilitate relative sliding motion of the concave surface 102 and the convex surface 122. In this regard, the layer of lubricant 142 may also prevent the formation of a vacuum between the concave surface 102 and the convex surface 122 which may otherwise occur under a relatively high axial load 34 that may compress the convex surface 122 into the concave surface 102 and which may undesirably prevent movement therebetween.

Figure 7:
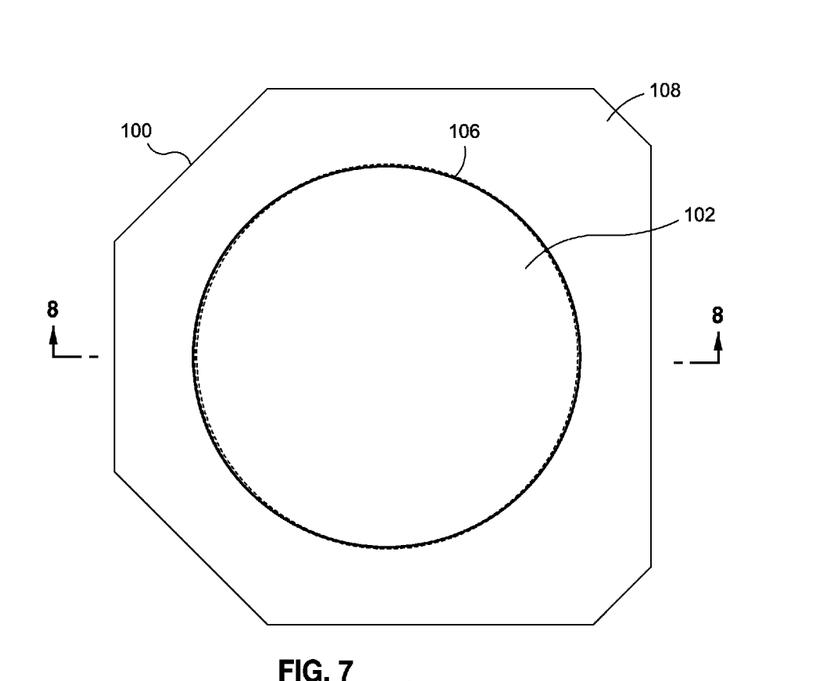
FIG. 7 is a top view of the first member illustrating the concave surface.
Figure 8:
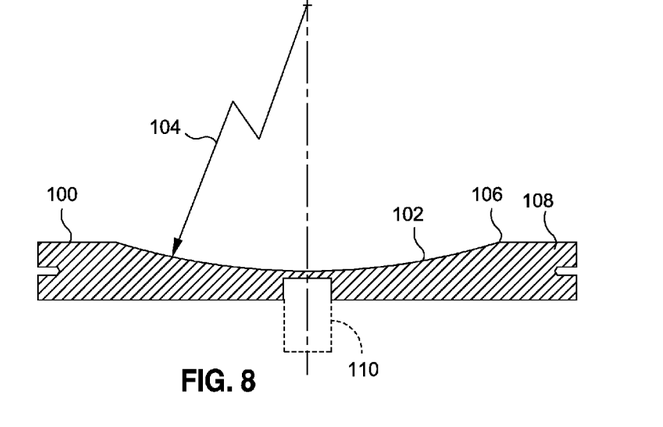
FIG. 8 is a cross sectional illustration of the first member taken along line 8 of FIG. 7.

Referring to FIGS. 7-8, shown is the first member 100 having the concave surface 102 formed generally in the center of the first member 100. The first member 100 may be formed of plate material and the concave surface 102 may be machined into the first member 100 or formed by other suitable means including by casting, electrical discharge machining (EDM), or any one of a variety of alternative fabrication techniques. FIG. 8 illustrates a bore formed in an underside of the first member 100 for receiving a centering pin 110 for coupling the first member 100 to the tabletop 16 (FIG. 3) of the universal testing machine (FIG. 3). The concave surface 102 defines a perimeter 106 having a perimeter flange 108 extending therearound.

Figure 9:
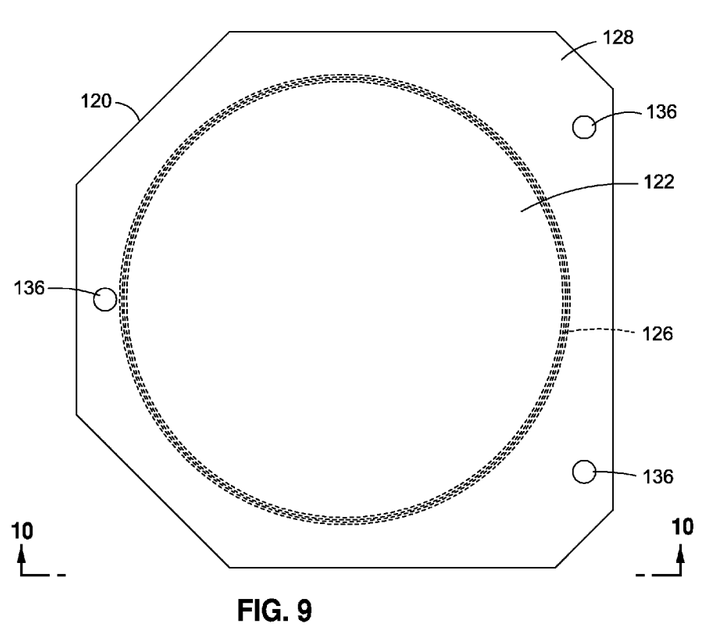
FIG. 9 is a top view of the second member illustrating the convex surface.

Referring to FIGS. 9-10, shown is the second member 120 having the convex surface 122 formed generally in the center of the second member 120. The second member 120 may also be formed of plate material wherein the convex surface 122 may be machined into the second member 120 or formed using other suitable techniques. Threaded bores 136 may be formed in the perimeter flange 128 surrounding the perimeter 126 of the convex surface 122. The threaded bores 136 may be configured for threadably receiving the positioning devices 160 (FIG. 6) such as the positioning screws 162 (FIG. 6). The second member 120 may include an undercut 134 (FIG. 10) extending around the convex surface 122 to form a shoulder around the perimeter 126 of the convex surface 122. The undercut 134 may facilitate manufacturing of the convex surface 122 by eliminating the need to blend the convex surface 122 into the generally planar perimeter flange 128 during the fabrication of the second member 120.

Figure 11:
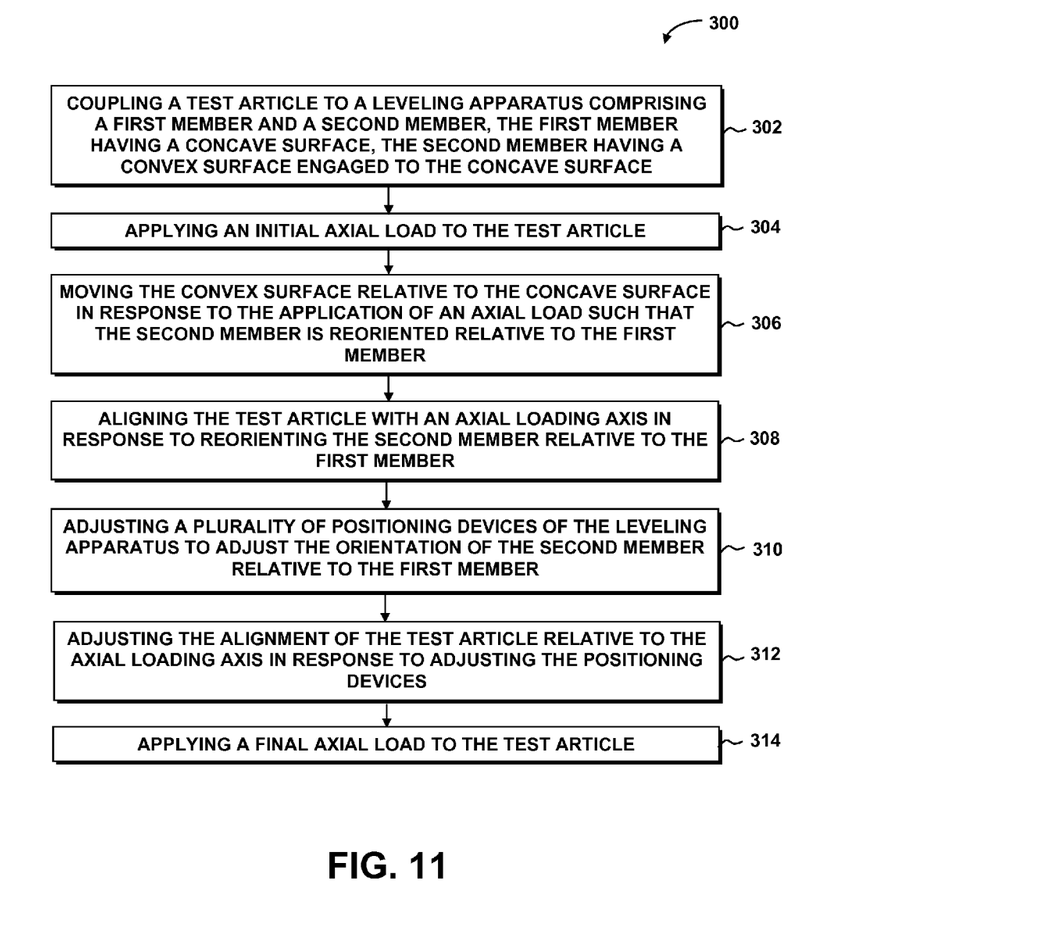
FIG. 11 is an illustration of a flowchart comprising one or more operations that may be included in a method for aligning a test article with a loading axis of a compression load applied by the universal testing machine.
Figure 12:
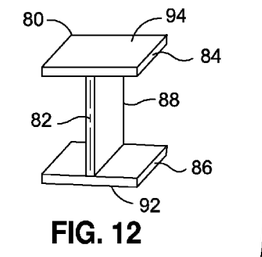
FIG. 12 is a perspective illustration of an embodiment of the test article.
Figure 13:
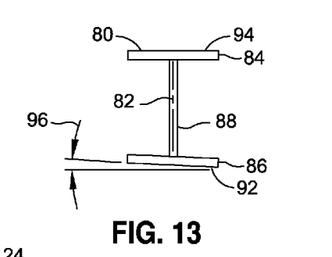
FIG. 13 is an end the view of the test article illustrating a lower flange of the test article oriented at an angular offset relative to the upper flange.
Figure 14:
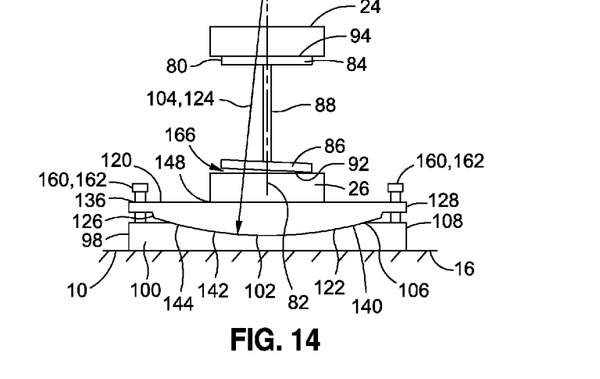
FIG. 14 is a schematic illustration of the test article mounted between the upper and lower loading plates and illustrating a gap between the lower flange and the lower loading plate.
Figure 15:
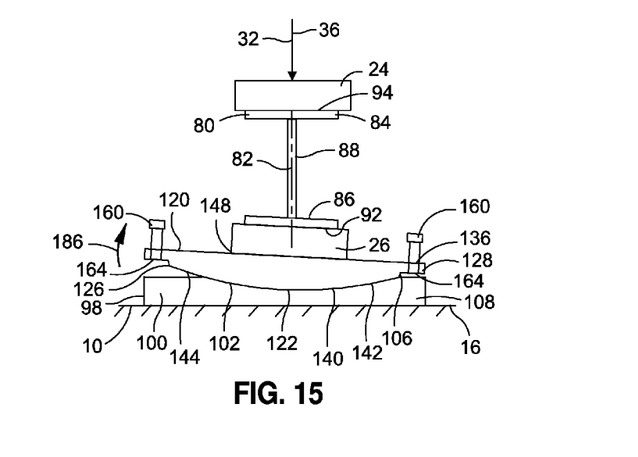
FIG. 15 is a schematic illustration of the test article having an initial axial load applied thereto and causing the second member to be reoriented relative to the first member.

Referring to FIG. 11 and with additional reference to the schematic illustrations of FIGS. 12 through 17, shown is a flow chart of a method 300 of aligning a test article 80 with an axial load 34 (FIG. 15) acting along an axial loading axis 32 (FIG. 15). The method may be implemented using the leveling apparatus 98 illustrated in FIGS. 4-10. The method 300 is described in the context of the I-beam-shaped test article 80 illustrated in FIGS. 12-13. However, as was indicated earlier, the leveling apparatus 98 may be implemented for aligning test articles of any size, shape and configuration, without limitation, and is not limited to the I-beam-shaped test article 80 illustrated in FIGS. 12-13. Furthermore, the leveling apparatus 98 is not limited to implementation in a testing machine 10 (FIG. 1) but may be incorporated into any system, subsystem, assembly, or process requiring the alignment of a component with a compressive loading axis. In FIG. 13, the test article 80 may have a proximal end 92 and a distal end 94 and wherein the proximal end 92 may be angularly offset 96 relative to the orientation of the distal end 94. It should be noted that although the angular offset 96 is exaggerated in FIG. 13, the angular offset 96 may be relatively small and may represent angularity in the test article 80 due to manufacturing tolerances and/or due to tolerances in the testing machine 10 (FIG. 1). Advantageously, the leveling apparatus 98 may prevent eccentric loading of the test article 80 that may otherwise occur due to the angular offset 96 of the proximal end 92.

Referring to FIG. 14, in Step 302 of the method 300 of FIG. 11, the leveling apparatus 98 may be installed between the tabletop 16 of the universal testing machine 10 and the lower loading plate 26. The test article 80 may be mounted between the upper loading plate 24 and the lower loading plate 26. However, as was indicated above, the test article 80 may be coupled directly to or mounted directly against the leveling apparatus 98 at the proximal end 92 of the test article 80. In addition, the distal end 94 of the test article 80 may be coupled directly to or mounted directly against the axial load actuator 28 (FIG. 3). The convex surface 122 of the second member 120 may be engaged to the concave surface 102 of the first member 100. The positioning devices 160 may be initially extended such that the tips 164 contact the first member 100 to prevent movement of the second member 120 relative to the first member 100 during initial mounting of the test article 80 between the upper and lower loading plates 24, 26. The angular offset 96 of the proximal end 92 of the test article 80 may result in a gap 166, shown exaggerated in FIG. 14, between the proximal end 92 of the test article 80 and the lower loading plate 26 as illustrated in FIG. 14.

Referring to FIG. 15, in Step 304 of the method 300 of FIG. 11, the positioning devices 160 may be retracted to allow for free movement of the first member 100 relative to the second member 120 after the test article 80 is mounted between the upper and lower loading plates 24, 26. In this regard, the positioning devices 160 may comprise positioning screws 162 which may be threadably retracted such that the tips 164 of the positioning screws 162 will not contact the first member 100. An initial axial load 36 may be applied to the test article 80. The initial axial load 36 may be of a relatively small magnitude such as approximately several hundred pounds or less, depending upon the relative size of the leveling apparatus 98, the relative size of the test article 80, and other factors. The initial axial load 36 is preferably of a magnitude to cause the second member 120 to be reoriented relative to the first member 100 such that any gaps 166 (FIG. 14) between the proximal end 92 of the test article 80 and the lower loading plate 26 are substantially eliminated. The initial axial load 36 may be applied by the axial load actuator 28 (FIG. 3) along the axial loading axis 32 (FIG. 3).

Step 306 of the method 300 of FIG. 11 may include slidably moving or rotating the convex surface 122 relative to the concave surface 102 along the interface 140 in response to the application of the initial axial load 36. The convex surface 122 may slidably move relative to the concave surface 102 such that the second member 120 may be reoriented 186 relative to the second member 120. Slidable movement of the convex surface 122 relative to the concave surface 102 may be facilitated by the lubricant 142 which may be installed in the interface 140 between the concave surface 102 and the convex surface 122. Slidable movement may also be facilitated between the convex surface 122 and the concave surface 102 by providing a relatively fine surface roughness of the concave surface 102 and the convex surface 122 to minimize friction.

Figure 17:
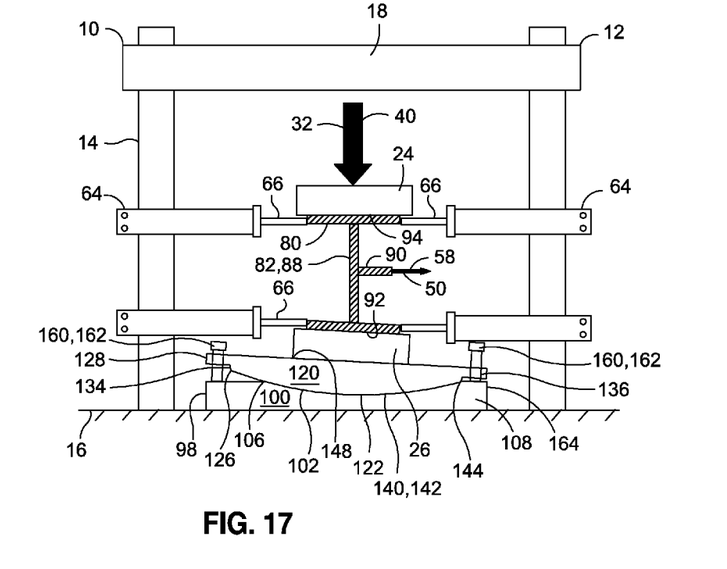
FIG. 17 is a schematic illustration of the test article mounted within a universal testing machine and illustrating a final axial load applied to the test article and a side load applied to the test article.

Step 308 of the method 300 of FIG. 11 may include generally aligning the test article 80 with the axial loading axis 32 in response to reorienting the second member 120 relative to the first member 100. In the configuration of the test article 80 shown, the axis 82 of the test article may be represented by the web 88 extending between the upper flange 84 and the lower flange 86 of the test article 80. For an arrangement where the web 88 is oriented generally perpendicular or normal to the upper flange 84, the reorientation of the second member 120 relative to the first member 100 during application of the initial axial load 36 may eliminate gaps 166 (FIG. 14) between the test article 80 and the upper and lower loading plates 24, 26 as the first and second member 100, 120 are reoriented relative to one another. In addition, the general alignment of the test article 80 with the axial loading axis 32 in response to reorienting the second member 120 relative to the first member 100 may prevent eccentric loading of the test article 80 during application of the final axial load 40 (FIG. 17).

Figure 16:
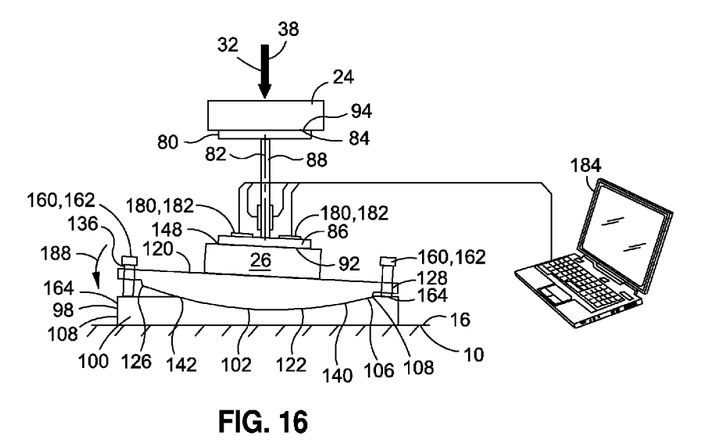
FIG. 16 is a schematic illustration of the test article having an intermediate axial load applied thereto and further illustrating a plurality of strain gauges mounted to the test article to measure stress in the test article to facilitate adjustment of the alignment of the test article relative to a loading axis by adjusting the positioning devices.

Referring to FIG. 16, Step 310 of the method 300 of FIG. 11 may include adjusting one or more of the positioning devices 160 of the leveling apparatus 98 as a means to adjust the orientation 188 of the second member 120 relative to the first member 100. The test article 80 may be instrumented with sensors 180 such as strain gauges 182 that may be mounted at predetermined locations on the test article 80. The strain gauges 182 may be coupled through appropriate electronic equipment (not shown) to a readout device 184 such as a portable computer for indicating and recording measurements of strain and/or stress in the test article 80 at the predetermined locations. An intermediate axial load 38 may be applied to the test article 80 in order to seat the convex surface 122 into the concave surface 102 and cause the first member 100 and the second member 120 to settle into an equilibrium orientation wherein relative movement of the first and second members 100, 120 is negligible or nonexistent. The intermediate axial load 38 may have a magnitude that is greater than the magnitude of the initial axial load 36. For example, the intermediate axial load 38 may have a magnitude of several thousand pounds although larger or smaller magnitude loads may be applied to the test article 80 during application of the intermediate axial load 38.

With the intermediate axial load 38 applied to the test article 80, strain or stress readings from the sensors 180 (e.g. strain gauges 182) may be monitored and compared to predicted strain or stress levels at the predetermined locations on the test article 80. The predicted stress levels may be determined based upon stress analysis of a fully supported test article 80 wherein no gaps 166 (FIG. 14) exist between the test article 80 and the upper and lower loading plates 24, 26 and no gaps exist between the upper and lower loading plates 24, 26 and the leveling apparatus 98 or between the leveling apparatus 98 and the tabletop 16. For a symmetrical test article 80 similar to the I-beam test article 80 configuration illustrated in FIG. 16, substantially equivalent strain or stress measurements at mirror image locations on opposite sides of the web 88 may provide an indication of a substantially uniform distribution of stress in the test article 80 as a result of the alignment of the test article 80 with the axial loading axis 32 as provided by the leveling apparatus 98. For a non-symmetrical test article (not shown), stress or strain measurements may be compared to predicted stress or strain levels to determine if such non-symmetrical test article is fully supported and is not eccentrically loaded or subjected to induced stress due to non-uniform support of the test article.

Referring to FIG. 16, Step 312 of the method 300 of FIG. 11 may include adjusting the alignment of the test article 80 relative to the axial loading axis 32 in response to the adjustment of the positioning devices 160. In this regard, the positioning devices 160 may be adjusted to minimize or eliminate differences in stress or strain measurements in the strain gauges 182 on opposite sides of the axis of the test article 80. For example, the positioning screws 162 may be adjusted until the tips 164 of the positioning screws 162 come into contact with the first member 100. With the intermediate axial load 38 applied to the test article 80, the positioning screws 162 may be adjusted until the strain gauges 182 on one side of the web 88 of the test article 80 indicate stress measurements that are substantially equivalent to stress measurements from the strain gauges 182 mounted on an opposite side of the web 88 of the test article 80. Alternatively, the positioning screws 162 may be adjusted until the measurements from the strain gauges 182 at predetermined locations are substantially equivalent to predicted strains or stresses at the predetermined locations for a fully supported test article. The process of measuring the stresses or strains in the test article 80 and adjusting the positioning screws 162 may be iteratively performed until the measured stress or strains are substantially equivalent to the predicted stresses or strains within a predetermined tolerance band. In this manner, the positioning devices 160 may facilitate adjustment of the alignment of the test article 80 relative to the axial loading axis 32.

In a further embodiment, the method 300 of FIG. 11 may include the installation of shims (not shown) between the test article 80 and the upper and/or loading plates 24, 26 to fill gaps (not shown) or local non-uniformities (not shown) in the surfaces of the test article 80 that are in contact with the upper and/or lower loading plates 24, 26. The installation of shims may be iteratively performed in conjunction with the adjustment of the positioning devices 160 until the stresses or strains measured by the strain gauges 182 are substantially equivalent to predicted stresses or strains in the test article 80.

Referring to FIG. 17, Step 314 of the method 300 of FIG. 11 may include applying a final axial load 40 to the test article 80 after the positioning devices 160 are adjusted to adjust the alignment of the test article 80. The final axial load 40 may simulate loads to which the test article 80 may be subjected during service and wherein such loads may be of a relatively large magnitude. Advantageously, the leveling apparatus 98 is configured to accommodate relatively large axial compression loads. For example, the leveling apparatus 98 may accommodate axial compression loads of several 100,000 pounds such as up to 700,000 pounds of axial compression load or greater. The test article 80 may be instrumented with a plurality of sensors 180 such as strain gauges 182 for measuring stress in the test article 80 during application of the final axial load 40. The final compressive axial load 40 may be statically applied or may be applied in numerous cycles during fatigue testing.

FIG. 17 further illustrates the application of a side load 50 to the test article 80 along a side loading axis 58. The side load 50 may be applied to the test article 80 simultaneous with the application of the final axial load 40. The side load 50 may be applied to the test article 80 to simulate an out-of-plane buckling condition of the web 88. The side load 50 may be applied to the web 88 of the test article 80 by the side load actuator 52 illustrated in FIG. 2 and described above. As shown in FIG. 2, the side load 50 may be reacted by one or more bumper assemblies 66 which may be coupled to the columns 14 of the universal testing machine 10 by a plurality of side load clamps 64. The side load 50 may be applied to the web 88 by means of a lug 90 which may extend laterally outwardly from the web 88 as shown in FIG. 2. A clevis fitting 62 may be coupled to the lug 90 for connecting the web 88 to the side load actuator 52. The positioning screws 162 of the leveling apparatus 98 may maintain the orientation of the first member 100 relative to the second member 120 during application of the side load 50 and the final axial load 40 and thereby prevent movement of the lower flange 86 in response to an out-of-plane bending condition of the web 88. The side load 50 may be applied during static testing and/or fatigue testing of the test article 80. Application of the final axial load 40 and/or side load 50 may be applied at different temperatures in order to determine the effect of temperature on the load-carrying capability of the test article 80.

Additional modifications and improvements of the present disclosure may be apparent to those of ordinary skill in the art. The particular combination of parts described and illustrated herein is intended to represent only certain embodiments of the present disclosure and is not intended to serve as limitations of alternative embodiments or devices within the spirit and scope of the disclosure.

What is claimed is:

1. A leveling apparatus for orienting a test article relative to a load acting along an axial loading axis, comprising:
   a first member having a concave surface;
   a second member having a convex surface configured to engage the concave surface in a manner such that the second member is movable relative to the first member, the test article being non-integral with the first and second members, the test article being coupled to one of the first and second members such that relative movement thereof facilitates general alignment of the test article with the axial loading axis;
   the first and second member being movable relative to one another to a reoriented position upon the application of an initial axial compressive load, and being maintained in the reoriented position thereafter without a tensioning stud extending through the first and second member; and
   a plurality of positioning devices configured to facilitate adjustment of an orientation of the first member relative to the second member for adjusting the alignment of the test article relative to the axial loading axis, the positioning devices preventing movement of the second member relative to the first member.

2. The leveling apparatus of claim 1, wherein:
   the concave and convex surfaces are sized and configured such that an interface between the concave and concave surface defines an interface perimeter circumscribing at least one of the following when the interface perimeter is viewed along the axial loading axis:
   an area of the test article in contact with the one of the first and second members;
   an area of a loading plate in contact with the one of the first and second members.

3. The leveling apparatus of claim 1, wherein:
   the positioning devices comprise positioning screws threadably engaged to a corresponding plurality of threaded bores extending through the second member.

4. The leveling apparatus of claim 1, wherein:
   the test article has a proximal end and a distal end;
   the proximal end being coupled to the leveling apparatus; and
   the concave and convex surface having a center of curvature located above the distal end.

5. The leveling apparatus of claim 1, wherein:
   the concave surface and the convex surface each having a perimeter; and
   the perimeter of the convex surface being larger than the perimeter of the concave surface.

6. The leveling apparatus of claim 1, further comprising:
   a layer of lubricant between the concave surface and the convex surface.

7. A testing machine for applying a compressive load to a test article, comprising:
   an axial actuator configured to apply a compressive load to a test article along an axial loading axis;
   a first member having a concave surface;
   a second member having a convex surface configured to engage the concave surface in a manner such that the second member is movable relative to the first member, the test article being non-integral with the first and second members, the test article being coupled to one of the first and second members such that relative movement thereof facilitates general alignment of the test article with the axial loading axis;
   the first and second member being movable relative to one another to a reoriented position upon the application of an initial axial compressive load, and being maintained in the reoriented position thereafter without a tensioning stud extending through the first and second member; and
   a plurality of positioning devices configured to facilitate adjustment of an orientation of the first member relative to the second member for adjusting the alignment of the test article relative to the axial loading axis, the positioning devices preventing movement of the second member relative to the first member.

8. The testing machine of claim 7, wherein:
   the concave and convex surface being sized and configured such that an interface between the concave and convex surface defines an interface perimeter circumscribing at least one of the following when the interface perimeter is viewed along a direction generally parallel to the axial loading axis:
   a portion of the test article in contact with at least one of the first and second members;
   a loading plate interposed between the test article and one of the first and second members.

9. The testing machine of claim 7, wherein:
   at least one of the first and second members includes at least three positioning devices for engaging an opposing one of the first and second members.

10. The testing machine of claim 9, wherein:
    the positioning devices comprise positioning screws threadably engaged to a corresponding plurality of threaded bores formed in one of the first and second members.

11. The testing machine of claim 7, wherein:
    the second member being movable relative to the first member in a manner to substantially align the axial load with an axis of the test article.

12. The testing machine of claim 7, wherein:
    the test article has a proximal end and a distal end;
    the proximal end being mounted to one of the first and second members; and
    the concave and convex surface having a center of curvature located approximately adjacent to the distal end of the test article.

13. The testing machine of claim 7, wherein:
    each one of the concave surface and convex surface having a perimeter; and
    the perimeter of the convex surface being larger than the perimeter of the concave surface.

14. The testing machine of claim 7, wherein:
    a layer of lubricant located between the concave surface and the convex surface.

15. A method of aligning a test article with a loading axis, comprising the steps of:
    coupling the test article to a leveling apparatus comprising a first member and a second member, the first member having a concave surface, the second member having a convex surface engaged to the concave surface, the test article being non-integral with the first and second members;
    applying an initial axial load to the test article;
    moving the convex surface relative to the concave surface in response to an application of the axial load such that the second member is reoriented relative to the first member;
    aligning the test article with the axial loading axis in response reorienting the second member relative to the first member;

adjusting at least one positioning device of the leveling apparatus to adjust an orientation of the second member relative to the first member and prevent movement of the second member relative to the first member; and adjusting the alignment of the test article relative to the axial loading axis in response to adjusting the positioning device.

16. The method of claim 15, further comprising the step of:
applying a final axial load to the test article having a magnitude greater than the initial axial load.

17. The method of claim 15, further comprising the step of:
providing the concave and convex surface in a size and configuration such that an interface of the concave and concave surface defines an interface perimeter circumscribing an area of the test article coupled to the leveling apparatus when viewed along the axial loading axis.

18. The method of claim 15, further comprising the step of:
providing the positioning device as a positioning screw.

19. The method of claim 15, wherein the test article has a proximal end and a distal end, the proximal end being coupled to the leveling apparatus, the method further comprising the step of:

forming the concave and convex surface with a center of curvature located above the distal end.

20. The method of claim 15, further comprising the steps of:

measuring stress in at least one location on the test article during application of the axial load; and adjusting the positioning device to adjust the alignment of the test article with the axial loading axis until a measured stress at the location is substantially equivalent to a predicted stress in the test article at the location.

* * * * *